(12) United States Patent
Zubiate et al.

(10) Patent No.: US 8,945,096 B2
(45) Date of Patent: Feb. 3, 2015

(54) EXTENDABLE ARTICULATED PROBE DEVICE

(75) Inventors: Brett Zubiate, Pittsburgh, PA (US); Howard Choset, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 599 days.

(21) Appl. No.: 12/996,337

(22) PCT Filed: Jun. 5, 2009

(86) PCT No.: PCT/US2009/046508
§ 371 (c)(1),
(2), (4) Date: Apr. 11, 2011

(87) PCT Pub. No.: WO2009/149421
PCT Pub. Date: Dec. 10, 2009

(65) Prior Publication Data
US 2011/0184241 A1 Jul. 28, 2011

Related U.S. Application Data

(60) Provisional application No. 61/059,171, filed on Jun. 5, 2008.

(51) Int. Cl.
*A61B 17/00* (2006.01)
*A61B 19/00* (2006.01)
(Continued)

(52) U.S. Cl.
CPC ............. *A61B 1/0055* (2013.01); *A61B 1/0057* (2013.01); *A61B 19/2203* (2013.01);
(Continued)

(58) Field of Classification Search
CPC ............... A61B 19/22; A61B 19/2203; A61B 2019/2242
USPC .............................................. 606/141, 130, 1
See application file for complete search history.

(56) References Cited

U.S. PATENT DOCUMENTS 3,060,972 A 10/1962 Sheldon
3,643,653 A 2/1972 Takahashi et al.
(Continued)

FOREIGN PATENT DOCUMENTS

EP 1927312 6/2008
WO 2006083306 A2 8/2006

OTHER PUBLICATIONS

Shammas et al., "New Joint Design for Three-dimensional Hyper Redundant Robots," International Conference on Robots and Systems, Las Vegas, NV, Oct. 2003.
(Continued)

*Primary Examiner* — Lynsey Crandall
*Assistant Examiner* — Sebastian X Lukjan
(74) *Attorney, Agent, or Firm* — Fox Rothschild LLP

(57) ABSTRACT

An articulate probe device includes a first mechanism, a second mechanism, and an overtube mechanism. The first mechanism includes a proximal link which is movable coupled to a first intermediate link, a plurality of intermediate links, and a distal link which is moveably coupled to a second one of the intermediate links. The second mechanism includes a proximal link which is movable coupled to a first intermediate link, a plurality of intermediate links, and a distal link which is moveably coupled to a second one of the intermediate links. The overtube mechanism includes a proximal link which is movable coupled to a first intermediate link, a plurality of intermediate links, and a proximal link which is moveably coupled to a second one of the intermediate links. Further, at least one of the first mechanism, second mechanism, and overtube mechanism is steerable and extendable beyond the other mechanisms.

43 Claims, 13 Drawing Sheets

(51) Int. Cl.
*A61B 17/10* (2006.01)
*A61B 1/005* (2006.01)

(52) U.S. Cl.
CPC ............... *A61B2019/2211* (2013.01); *A61B 2017/00314* (2013.01); *A61B 2017/00323* (2013.01); *A61B 2019/2238* (2013.01)
USPC .............................. 606/1; 606/130; 606/141

(56) References Cited

U.S. PATENT DOCUMENTS

| | | | |
|---|---|---|---|
| 4,726,355 A | 2/1988 | Okada | |
| 5,143,475 A | 9/1992 | Chikama | |
| 5,251,611 A | 10/1993 | Zehel et al. | |
| 5,318,526 A | 6/1994 | Cohen | |
| 5,327,905 A | 7/1994 | Avitall | |
| 5,386,741 A | 2/1995 | Rennex | |
| 5,467,763 A | 11/1995 | McMahon et al. | |
| 5,472,017 A | 12/1995 | Kovalcheck | |
| 5,483,951 A | 1/1996 | Frassica et al. | |
| 5,514,157 A | 5/1996 | Nicholas et al. | |
| 5,531,715 A | 7/1996 | Engelson et al. | |
| 5,549,542 A | 8/1996 | Kovalcheck | |
| 5,605,543 A | 2/1997 | Swanson | |
| 5,662,587 A | 9/1997 | Grundfest et al. | |
| 5,743,876 A | 4/1998 | Swanson | |
| 5,759,151 A | 6/1998 | Sturges | |
| 6,036,677 A | 3/2000 | Javier, Jr. et al. | |
| 6,197,017 B1 | 3/2001 | Brock et al. | |
| 6,221,061 B1 | 4/2001 | Engelson et al. | |
| 6,432,112 B2 | 8/2002 | Brock et al. | |
| 6,517,477 B1 | 2/2003 | Wendlandt | |
| 6,554,844 B2 | 4/2003 | Lee et al. | |
| 6,610,007 B2 | 8/2003 | Belson et al. | |
| 6,623,448 B2 | 9/2003 | Slater | |
| 6,638,266 B2 | 10/2003 | Wilson et al. | |
| 6,682,493 B2 | 1/2004 | Mirigian | |
| 6,692,485 B1 | 2/2004 | Brock et al. | |
| 6,697,048 B2 | 2/2004 | Rosenberg et al. | |
| 6,730,020 B2 | 5/2004 | Peng et al. | |
| 6,790,173 B2 | 9/2004 | Saadat et al. | |
| 6,800,056 B2 | 10/2004 | Tartaglia et al. | |
| 6,827,710 B1 | 12/2004 | Mooney et al. | |
| 6,837,846 B2 | 1/2005 | Jaffe et al. | |
| 6,837,847 B2 | 1/2005 | Ewers et al. | |
| 6,858,005 B2 | 2/2005 | Ohline et al. | |
| 6,869,396 B2 | 3/2005 | Belson | |
| 6,890,297 B2 | 5/2005 | Belson | |
| 6,899,673 B2 | 5/2005 | Ogura et al. | |
| 6,907,298 B2 | 6/2005 | Smits et al. | |
| 6,960,162 B2 | 11/2005 | Saadat et al. | |
| 6,960,163 B2 | 11/2005 | Ewers et al. | |
| 6,963,792 B1 | 11/2005 | Green | |
| 6,974,411 B2 | 12/2005 | Belson | |
| 6,976,991 B2 | 12/2005 | Hebert et al. | |
| 6,984,203 B2 | 1/2006 | Tartaglia et al. | |
| 7,029,435 B2 | 4/2006 | Nakao | |
| 7,041,052 B2 | 5/2006 | Saadat et al. | |
| 7,044,907 B2 | 5/2006 | Belson | |
| 7,087,013 B2 | 8/2006 | Belson et al. | |
| 7,090,637 B2 | 8/2006 | Danitz et al. | |
| 7,090,683 B2 | 8/2006 | Brock et al. | |
| 7,108,688 B2 | 9/2006 | Jensen | |
| 7,128,708 B2 | 10/2006 | Saadat et al. | |
| 7,169,141 B2 | 1/2007 | Brock et al. | |
| 7,171,279 B2 | 1/2007 | Buckingham et al. | |
| 7,182,731 B2 | 2/2007 | Nguyen et al. | |
| 7,214,230 B2 | 5/2007 | Brock et al. | |
| 7,232,434 B2 | 6/2007 | Suyama et al. | |
| 7,250,027 B2 | 7/2007 | Barry | |
| 7,322,935 B2 | 1/2008 | Palmer et al. | |
| 7,338,505 B2 | 3/2008 | Belson | |
| 2004/0116832 A1* | 6/2004 | Friedrich et al. | 600/585 |
| 2004/0138525 A1 | 7/2004 | Saadat et al. | |
| 2004/0138529 A1* | 7/2004 | Wiltshire et al. | 600/144 |
| 2005/0240078 A1 | 10/2005 | Kwon et al. | |
| 2006/0025752 A1* | 2/2006 | Broaddus et al. | 604/537 |
| 2008/0039169 A1 | 2/2008 | Zubiate et al. | |
| 2008/0065099 A1* | 3/2008 | Cooper et al. | 606/130 |
| 2009/0171151 A1 | 7/2009 | Choset et al. | |

OTHER PUBLICATIONS

Brown et al., "Design and Control of a Second-Generation Hyper-Redundant Mechanism," International Conference on Robots and Systems, San Diego, CA, Oct. 29-Nov. 2, 2007.

Wolfe et al., "A Mobile Hyper Redundant Mechanism for Search and Rescue Tasks," International Conference on Robots and Systems, Las Vegas, NV, Oct. 2003.

* cited by examiner

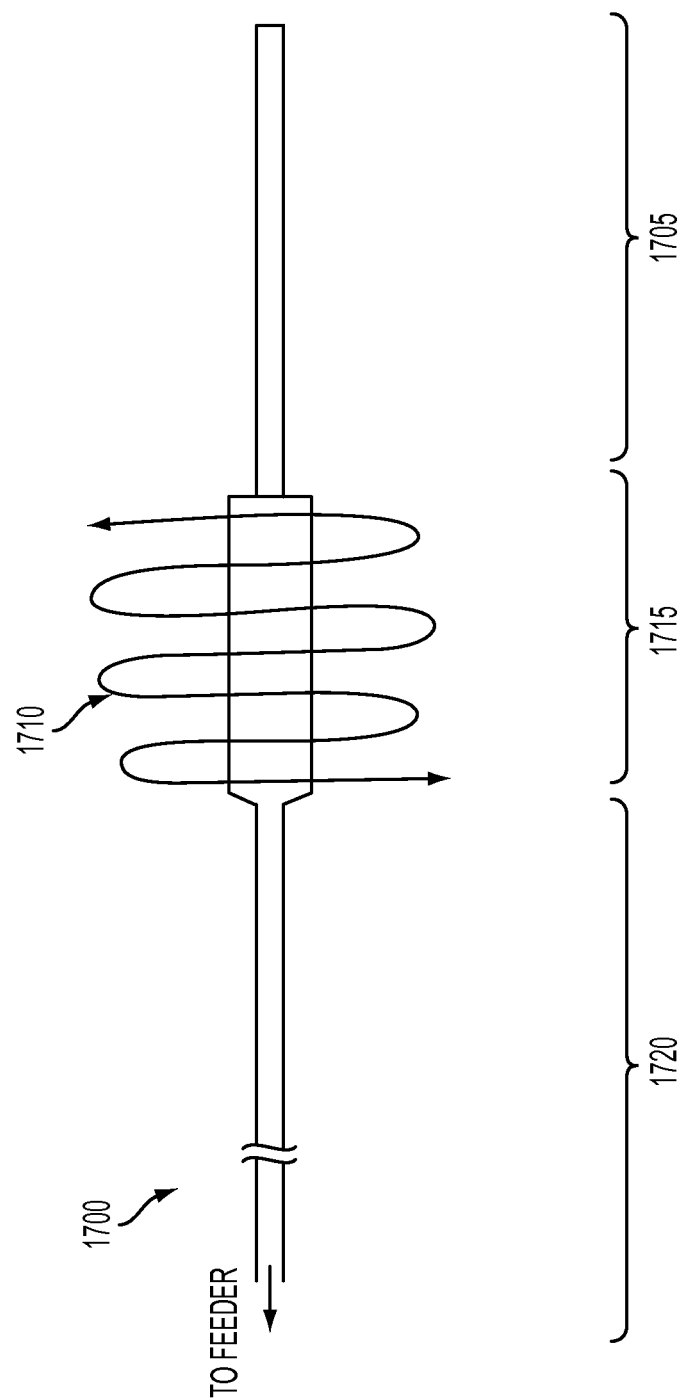

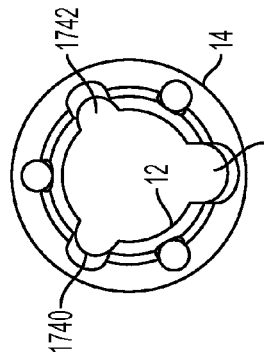
FIG. 13H
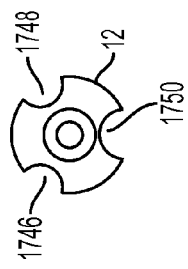
FIG. 13I
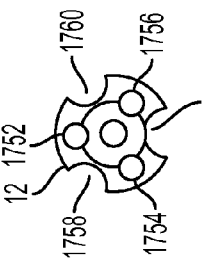
FIG. 13J
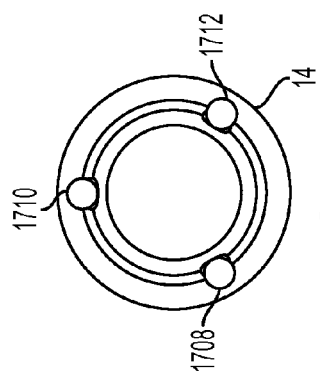
FIG. 13B
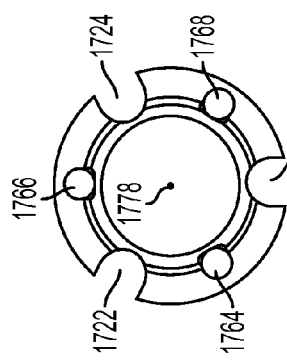
FIG. 13D
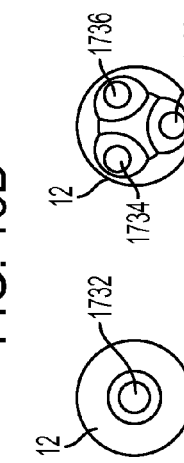
FIG. 13G
FIG. 13F
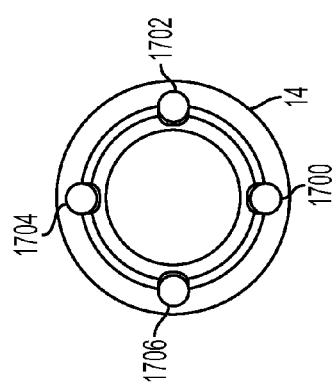
FIG. 13A
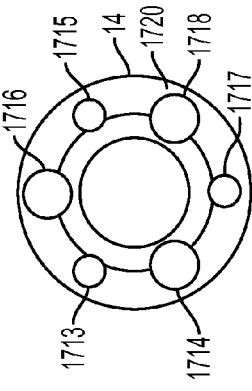
FIG. 13C
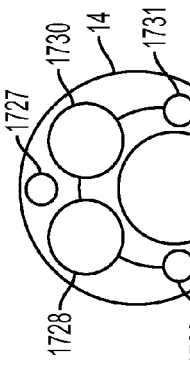
FIG. 13E

EXTENDABLE ARTICULATED PROBE DEVICE

CROSS REFERENCE TO RELATED APPLICATIONS

This application claims the benefit of the filing date of, and priority to, U.S. Provisional Patent Application No. 61/059,171 filed Jun. 5, 2008.

BACKGROUND

This application discloses an invention that is related, generally and in various embodiments, to a multi-linked robotic device, a continuum robot, or other highly articulated device. This device may be used to deliver a tool such as a camera, probe, scalpel or other tool to an area of interest inside a patient's body during a surgical procedure. For minimally invasive procedures, such as cardiac ablation, a minimally complex articulated device is usually sufficient. However, for more complex procedures, a longer device may be necessary. A longer mechanism may require extra support along at least a portion of its length to counteract any increased loading. In addition, the device may need to accommodate additional tools needed to perform certain parts of a more complex procedure.

SUMMARY

Before the present methods are described, it is to be understood that this invention is not limited to the particular systems, methodologies or protocols described, as these may vary. It is also to be understood that the terminology used herein is for the purpose of describing particular embodiments only, and is not intended to limit the scope of the present disclosure which will be limited only by the appended claims.

It must be noted that as used herein and in the appended claims, the singular thrills "a," "an," and "the" include plural reference unless the context dead dictates otherwise. Unless defined otherwise, all technical and scientific terms used herein have the same meanings as commonly understood by one of ordinary skill in the art. As used herein, the term "comprising" means "including, but not limited to."

In one general respect, the embodiments disclose an articulated probe device. The articulate probe device includes a first mechanism, a second mechanism, and at least one overtube mechanism. More specifically, the first mechanism includes a first link positioned at a proximal area of the first mechanism, a plurality of intermediate links, wherein a first one of the intermediate links is moveably coupled to the first link, and a second link positioned at a distal area of the second mechanism which is moveably coupled to a second one of the intermediate links. The second mechanism includes a first link positioned at a proximal area of the second mechanism, a plurality of intermediate links, wherein a first one of the intermediate links is moveably coupled to the first link, and a second link positioned at a distal area of the second mechanism and which is moveably coupled to a second one of the intermediate links. The at least one overtube includes a first link positioned at a proximal area of the overtube mechanism, a plurality of intermediate links, wherein a first one of the intermediate links is moveably coupled to the first link, and a second link which is moveably coupled to a second one of the intermediate links and positioned at a proximal area of the overtube mechanism. Further, at least one of the first mechanism, second mechanism, and overtube mechanism is configured to be steerable and extendable beyond the other mechanisms.

BRIEF DESCRIPTION OF DRAWINGS

Various embodiments of the invention are described herein by way of example in conjunction with the following figures.

FIG. 12 illustrates an exemplary tensioning cables and splice according to an embodiment.

FIG. 13A-13J illustrate exemplary port and through-hole configurations are according to an embodiment.

DETAILED DESCRIPTION

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

According to various embodiments, the invention described herein may be utilized to control movement of an articulated device, which in the figures and description herein is described as a steerable multi-linked device. In an embodiment, a surgical probe may be an exemplary articulated device. A surgical probe may be used to perform surgical procedures, exploratory procedures and/or the like on humans and/or animals. For ease of explanation purposes, the invention will be described in the context of its use with various embodiments of the steerable multi-linked device described herein. However, one skilled in the art will appreciate that the invention may be utilized with other types of multi-linked devices as well as other types of devices such as, but not limited to, endoscopes, highly articulated devices and/or the like.

Figure 1:
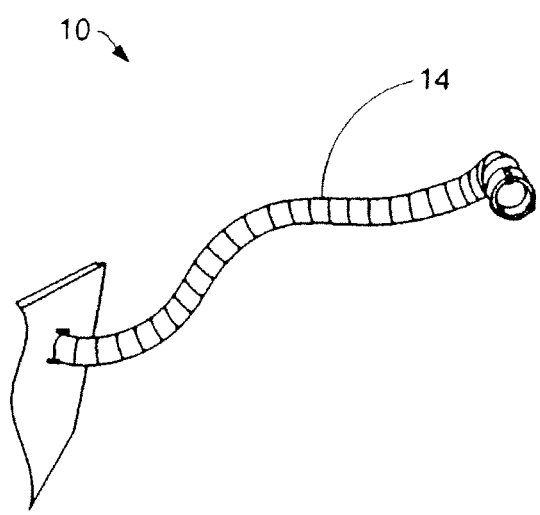
FIGS. 1 and 2 illustrate various embodiments of a steerable multi-linked device.

FIG. 1 illustrates a representative embodiment of a highly articulated extendible probe device 10. The cross-section of such an embodiment is depicted in FIG. 1. According to the representative embodiment, the device may be a steerable device such as a snake-like robot, a continuum robot or the like. Various embodiments of the device 10 may be utilized for medical procedures (e.g., as a robotic bore, positioning device, ablation tool, camera or instrument support, or guidance system for minimally invasive procedures), for surveillance applications, for inspection applications, for search and rescue applications, etc. For purposes of clarity only, the utility of the device 10 will be described hereinbelow in the context of its applicability to medical procedures. However, a person skilled in the art will appreciate that the device 10 can be utilized in a variety of different applications.

Figure 2:
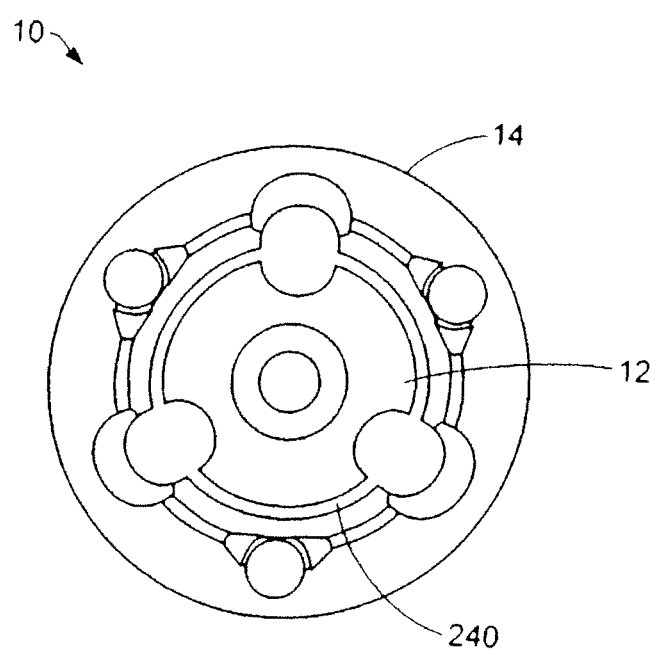

The device 10 comprises a first mechanism 12 and a second mechanism 14. According to the representative embodiment, a mechanism may be a series of articulated links, a snake-like robot, a continuum robot or the like. According to the representative embodiment, the second mechanism 14 is structured and arranged to receive and surround the first mechanism 12 as shown in FIG. 2. Thus, the first mechanism and second mechanism may be concentric. According to other embodiments, the first and second mechanisms 12, 14 may be structured and arranged to have a relationship other than a concentric relationship. For example, the second mechanism 14 may surround the first mechanism 12, however, the first mechanism 12 may be arranged eccentrically with respect to the second mechanism 14. According to the representative embodiment, the first and second mechanisms 12, 14 may be structured and arranged to operate in a side-by-side arrangement, where the first mechanism 12 operates alongside the second mechanism 14. According to the representative embodiment, additional and/or alternate configurations may be used within the scope of this disclosure. According to the representative embodiment, a gap or three-dimensional space 240 may be provided between the first and second mechanisms. This space will be described in more detail below.

As described in more detail hereinbelow, the first mechanism 12 may operate in either a rigid mode or a limp mode, the second mechanism 14 may operate in either a rigid mode or a limp mode, and the first and second mechanisms 12, 14 may operate independent of one another. At least one of the mechanism is rigid at all times during operation of the device 10. Both the first mechanism 12 and the second mechanism 14 may be steerable mechanisms. Accordingly, it will be appreciated that the device 10 may be utilized to navigate a luminal space as well as any path within a three-dimensional intracavity space, void, or an otherwise unconstrained three-dimensional volume. According to the representative embodiment, the device 10 may advance by alternating the operation of the first mechanism 12 and the second mechanism 14 between a limp mode and a rigid mode. Further, both mechanisms can both exist in the rigid mode at the same time.

According to the representative embodiment, the device 10 may also comprise one or more cables. According to the representative embodiment, one or more of the cables 10 may be steering cables and/or tensioning cables. For example, the device 10 may include three cables fast steering disposed through the second mechanism and one cable for tensioning which is disposed through the first mechanism. Alternatively, the device 10 may include four steering cables. More, fewer, alternative and/or additional cables may be used within the scope of this disclosure.

Figure 3:
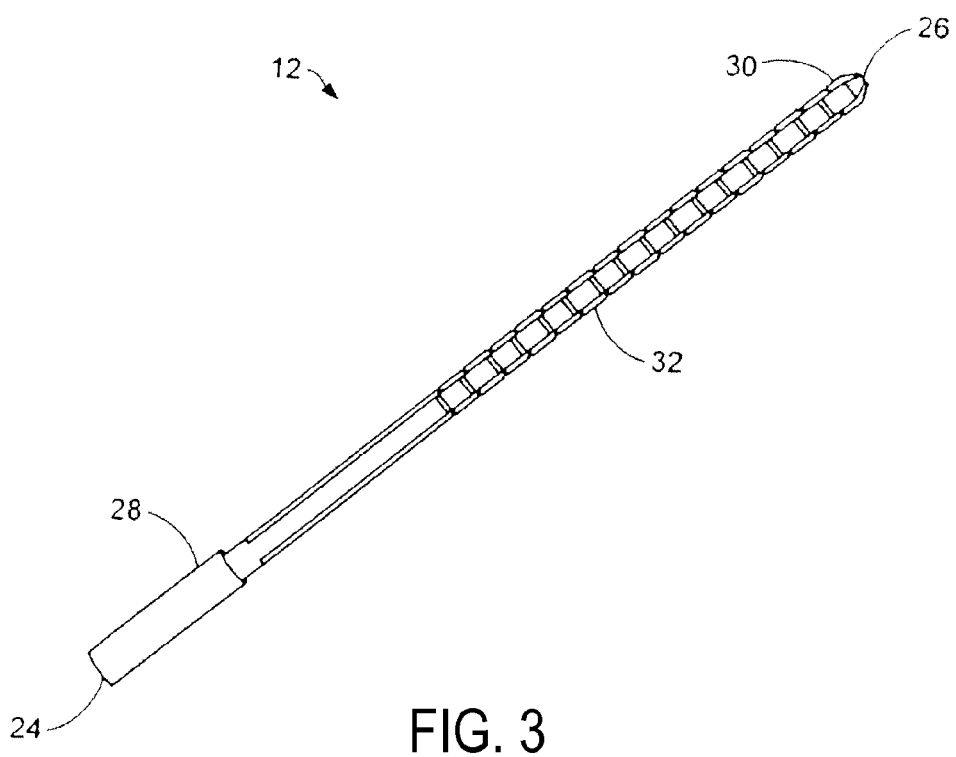
FIG. 3 illustrates various embodiments of a core mechanism of the device of FIG. 1.

FIG. 3 illustrates various embodiments of either mechanism of the device. Shown in FIG. 3 is the first mechanism 12 of the device 10. The first mechanism 12 is a multi-linked mechanism and includes a first end 24 and a second end 26. The first end 24 may be considered the proximal end and the second end 26 may be considered the distal end. The first mechanism 12 may comprise a first link 28, a second link 30, and one or more intermediate links 32 between the first and second links 28, 30. The first link 28 may be considered the proximal link, and the second link 30 may be considered the distal link. Any link between the proximal link 28 and distal link 30 may be considered an intermediate link 32. Exemplar link structures are shown in, for example, U.S. Patent Application Publication No. 2008/0039690.

Figure 4:
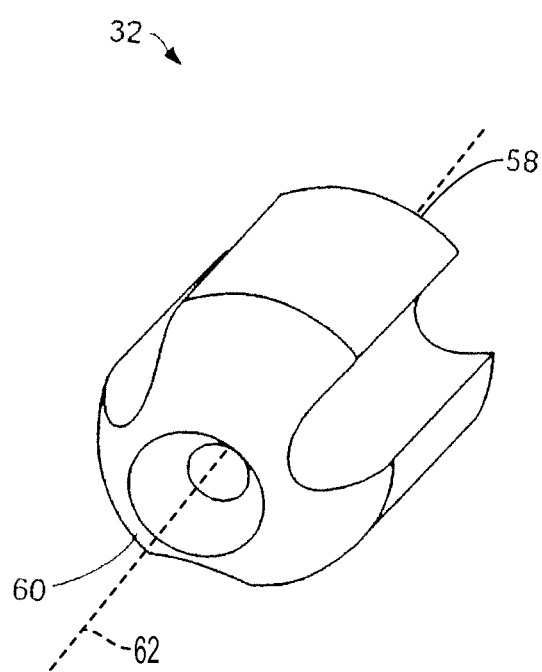
FIGS. 4 and 5 illustrate various embodiments of an intermediate link of the core mechanism.
Figure 5:
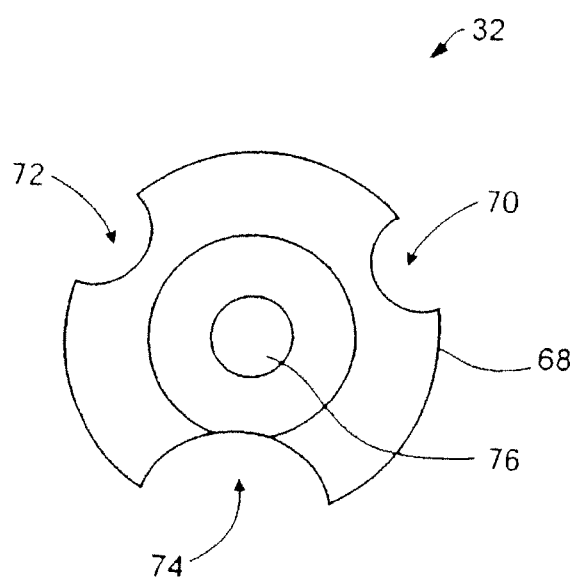

FIGS. 4 and 5 illustrate various views of an exemplary intermediate link 32 of the first mechanism 12 in an embodiment where the inner mechanism serves as the core. The intermediate link 32 is representative of the other intermediate links 32. The intermediate link 32 includes a first end 58 and a second end 60, and defines a longitudinal axis 62 that passes through the center of the first end 58 and the center of the second end 60. Link 32 includes a passage 76 or through-hole which may be positioned along the longitudinal axis, or it may be positioned elsewhere in the link parallel to, or substantially parallel to, the longitudinal axis.

As shown in FIG. 4, the intermediate link 32 also comprises a first surface 68 that extends from the first end 58 of the intermediate link 32 to the second end 60 of the intermediate link 32. The first surface 68, shown in FIG. 5, may be considered the outer surface of the intermediate link 32. The intermediate link 32 also defines one or more port portions, referred to herein as grooves. In the example shown, link 32 includes a first groove 70 parallel to the longitudinal axis 62 along the first surface 68, a second groove 72 parallel to the longitudinal axis 62 along the first surface 68, and a third groove 74 substantially aligned to the longitudinal axis 62 along the first surface 68. Each of the first, second and third grooves 70, 72, 74 extend along the first surface 68 from the first end 58 of the intermediate link 32 toward the second end 60 of the intermediate link 32. The first, second and third grooves 70, 72, 74 may be semi-tubular shaped and may be arranged in a radially symmetric manner around the longitudinal axis 62 on the first surface 68 of the intermediate link 32 as shown in FIGS. 4 and 5. The size of each of the grooves 70, 72, 74 may be identical to one another or may be different from one another. For example, according to various embodiments, the first and second grooves 70, 72 are configured as segments of a cylinder having a diameter on the order of approximately 1.75 millimeters at the first end 58 of the intermediate link 32, and the third groove 74 is configured as a segment of a cylinder having a diameter on the order of approximately 2.50 millimeters at the first end 58 of the intermediate link 32. The first, second and third grooves 70, 72, 74 are each configured to provide a portion of a port structure.

The intermediate link 32 also defines a through-hole or passage 76 extending from the first end 58 to the second end 60 and is parallel to the longitudinal axis. The through-hole or passage 76 may be of a size sufficient to allow one or more cables to pass there-through.

Figure 6:
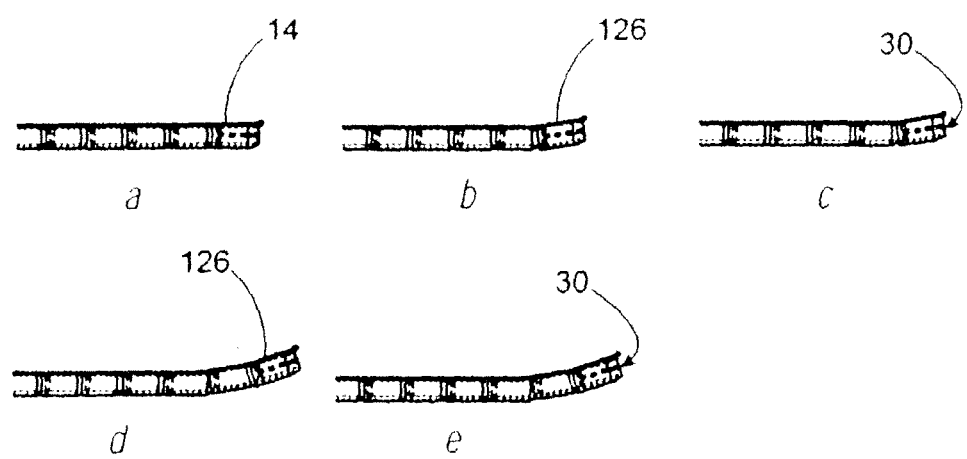
FIG. 6 illustrates various embodiments of a motion sequence of the device of FIG. 1.

FIG. 6 illustrates various steps of a motion sequence of the steerable multi-linked device 10. At the start of the sequence, the second mechanism 14 surrounds the first mechanism 12 as shown in step "a" of FIG. 6, the longitudinal axes of the links 28, 30, 32 of the first mechanism 12 are substantially aligned with the respective longitudinal axes 134, 164, 212 of the links (e.g., link 126) of the second mechanism, and the second end 26 of the first mechanism 12 is at substantially the same position as the second end 122 of the second mechanism 14. A tensioning cable passes through a through-hole of the first mechanism. It is terminated on an actuation component at the proximal area or end of the first mechanism and at a next-to-last link at as distal end. The tensioning cable is pulled tight, thereby placing, at least a portion of the first mechanism 12 in the rigid mode by placing a force on the distal link and at least a some intermediate links. The steering cables are not pulled tight, thereby placing the second mechanism 14 in the limp mode.

The second mechanism 14 is then advanced, so that its second link 126 is positioned approximately one link ahead of the second end 24 of the first mechanism 12 as shown in step of FIG. 6. The cables 16, 18, 20 may be utilized to orient the second link 126 to a particular orientation, where the longitudinal axis 134 of the first link 124 is no longer aligned with the longitudinal axes 164 of the intermediate links 128 of the second mechanism 14 or the longitudinal axis 90 of the second link 30 of the first mechanism 12. After the second link 126 is in the desired position and orientation, the steering cables are pulled with appropriate forces in order to place the second mechanism 14 in the rigid mode, thereby preserving the position and orientation of the second mechanism 14 when the first mechanism is made limp.

The pulling three of the tensioning cable is then released to place the first mechanism 12 in the limp mode. After the first mechanism 12 is placed in the limp mode, the first mechanism 12 is advanced so that its second link 30 is at substantially the same position as the second end 122 of the second mechanism 14 as shown in step "c" of FIG. 6. After the second link 30 of the first, mechanism 12 is in the desired position, the tensioning cable is pulled tight to place the first mechanism 12 back in the rigid mode, thereby preserving the position and orientation of the first mechanism 12.

The pulling forces of the steering cables are then released to place the second mechanism 14 back in the limp mode. After the second mechanism 14 is placed back in the limp mode, the second mechanism 14 is advanced so that its second link 126 is once again positioned approximately one link ahead of the second end 26 of the first mechanism 12 as shown in step "d" of FIG. 6. After the second link 126 is in the desired position and orientation, the steering cables are pulled with identical force in order to place the second mechanism 14 in the rigid mode, thereby preserving the position and orientation of the second mechanism 14.

The pulling force of the tensioning cable is then released to place the first mechanism 12 back in the limp mode. After the first mechanism 12 is placed back in the limp mode, the first mechanism 12 is advanced so that its second link 30 is once again at substantially the same position as the second end 122 of the second mechanism 14 as shown in step "e" of FIG. 6. After the second link 30 of the first mechanism 12 is in the desired position and orientation, the tensioning cable is pulled tight to place the first mechanism 12 back in the rigid mode, thereby preserving the position and orientation of the first mechanism 12.

In an embodiment, the flexible, snake-like device 10 may include one or more overtubes. In an embodiment, an overtube may include a series of links in a similar fashion to the second mechanism. In an embodiment, an overtube may be a snake-like robot, a continuum robot or the like. An overtube may be fabricated from metal, plastic, fiber, reinforced fiber, any combination thereof and/or the like.

In an embodiment, an overtube may include one or more through-holes. A through-hole may extend along a length of the overtube. In an embodiment, a through-hole may be substantially cylindrically shaped. A through-hole may be configured to surround and receive a cable. For example, as illustrated by FIG. 13, a through-hole 1800 may receive a steering cable 1805. In an embodiment, a steering cable may assist in controlling and guiding the movement of an overtube.

Figure 7:
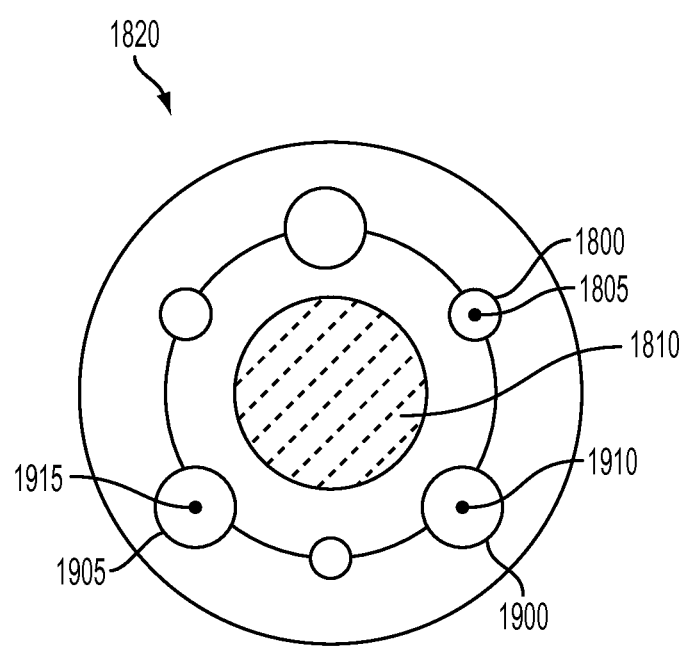
FIG. 7 illustrates an exemplary cross-section elan overtube according to an embodiment.

In an embodiment, an overtube 1820 may include one or more grooves, such as the grooves described above with respect to the intermediate link 32. The grooves of an overtube may align with grooves on the outside of a second mechanism to form one or more ports such as port 1900. A port may be a passageway that extends along, a length of a device. In an embodiment, an overtube may wholly contain one or more ports. In an embodiment, ports may be configured to surround and receive one or more tools. Additionally, overtube 1820 may include one or more through-holes 1800. For example, FIG. 7 illustrates an exemplary through-hole 1905 receiving a tensioning cable 1915 and an exemplary port 1900 receiving a tool 1910.

Figure 9:
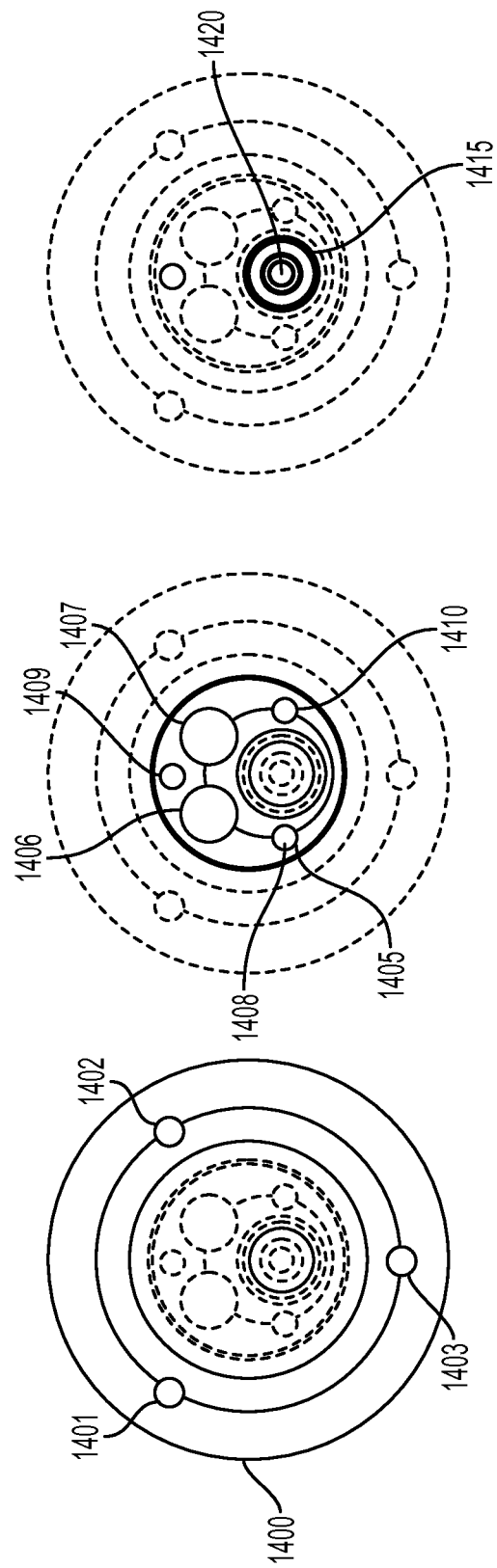
FIGS. 9A-9C illustrates exemplary cross-sections of a steerable multi-linked device haying an overtube according to an embodiment.

In an embodiment, an overtube may surround both the first mechanism 12 and the second mechanism 14. For example, as illustrated by FIGS. 9A-9C, the second mechanism 1405 may surround the first mechanism 1415, and the overtube 1400 may surround, the second mechanism 1405. In an embodiment, as shown in FIG. 2, the first mechanism 12 may be positioned concentrically with respect to the second mechanism 14. Alternatively, as shown in FIGS. 9A-9C, the first mechanism 1415 may be positioned eccentrically with respect to the second mechanism 1405. For example, the first mechanism 1415 may be located off-center from the second mechanism 1405. In an embodiment, the second mechanism 1405 may be positioned concentrically with respect to the overtube 1400. Alternatively, the second mechanism 1405 may be positioned eccentrically with respect to the overtube 1400. In an embodiment, the overtube may be fabricated from plastic, such as polysulfone and/or the like.

In an embodiment, the first mechanism 1415 and the second mechanism 1405 may be collectively considered an inner mechanism, and the overtube 1400 may be considered an outer mechanism. In an embodiment, the device may operate in a first mode. The first mechanism 1415 and the second mechanism 1405 may operate substantially in unison and both mechanisms may alternate between a rigid and a limp state together. The operation of the first mechanism 1415 and second mechanism 1405 may be complimentary to the overtube 1400. For example, the first mechanism 1415 and the second mechanism 1405 may both be made limp while the overtube 1400 is made rigid. Alternatively, the first mechanism 1415 and the second mechanism 1405 may both be made rigid when the overtube 1400 is made limp. Still further, the all mechanism may be made rigid at the same time.

For example, while in a limp state, the first mechanism 1415 and second mechanism 1405 may advance into the overtube 1400 to a certain position. The first mechanism 1415 and the second mechanism 1405 may be made rigid, while the overtube 1400 may be made limp. The overtube 1400 may advance over the first mechanism 1415 and the second mechanism 1405. This motion sequence is analogous to the motion sequence describe above and depicted in FIG. 6.

Figure 8:
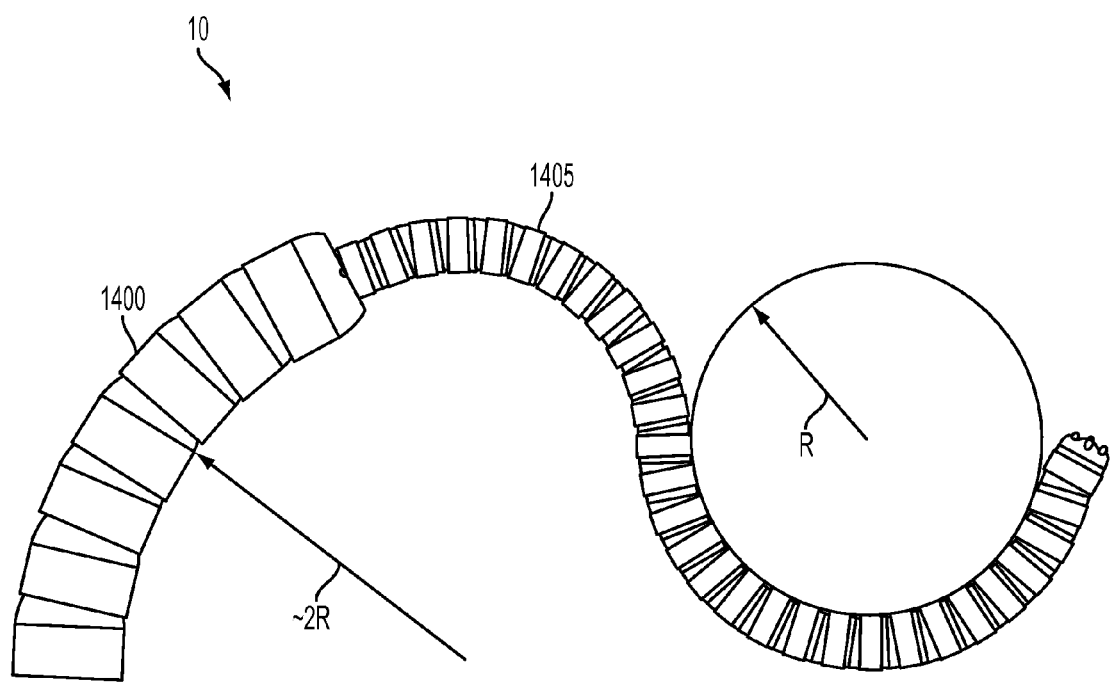
FIG. 8 illustrates an exemplary steerable multi-linked device having an overtube according to an embodiment.

In an embodiment, the device may operate in a second mode. In a second mode, the overtube 1400 may act as a steerable cannula that may be positioned with assistance from the first mechanism 1415 and the second mechanism 1405. For example, after reaching a target location, the overtube 1400 may be made rigid. The first mechanism 1415 and second mechanism 1405 may continue to advance, while the overtube 1400 may remain stationary. As illustrated in FIG. 8, the overtube 1400 may provide additional length to the flexible, snake-like device 10, allowing for more flexibility in its positioning and use. The overtube 1400 may also provide additional support to the first mechanism (contained within the second mechanism 1405) and the second mechanism 1405. As illustrated by FIG. 7, the radius of curvature associated with an overtube 1400 may, in some embodiments, be at least as large as the radius of curvature associated with the second mechanism 1405.

FIGS. 9A-9C illustrate exemplary cross-sections of an articulated device having an overtube according to an embodiment. In FIG. 9A, a cross-section of an overtube 1400 is highlighted. As illustrated by FIG. 9A, an overtube 1400 may include one or more through-holes 1401, 1402, 1403. Steering cables used to control the overtube 1400 may be received by the through-holes 1401, 1402, 1403.

In FIG. 9B, a cross-section of as second mechanism 1405 is highlighted. As illustrated by FIG. 9B, a second mechanism 1405 may include one more through-holes 1408, 1409, 1410. Steering cables used to control movement of the second mechanism 1405 may be received by the through-holes 1408, 1409, 1410. In an embodiment, the second mechanism 1405 may include one or more ports 1406, 1407. A port may be a passageway that extends along the length of a device. In an embodiment, a port may be formed by the alignment of one or more grooves of a first mechanism and one or more grooves or walls of a second mechanism. In an alternate embodiment shown in FIG. 9B, a port may be wholly formed in a first mechanism and/or a second mechanism. In an embodiment, one or more through-holes may be configured to surround and receive one or more tensioning cables and at least one port may be configured to surround tools and for the like.

In FIG. 9C, a cross-section of the first mechanism 1415 is highlighted. As illustrated, by FIG. 9C, a first device 1415 may include a through-hole 1420 for delivery of a tool.

Figure 10:
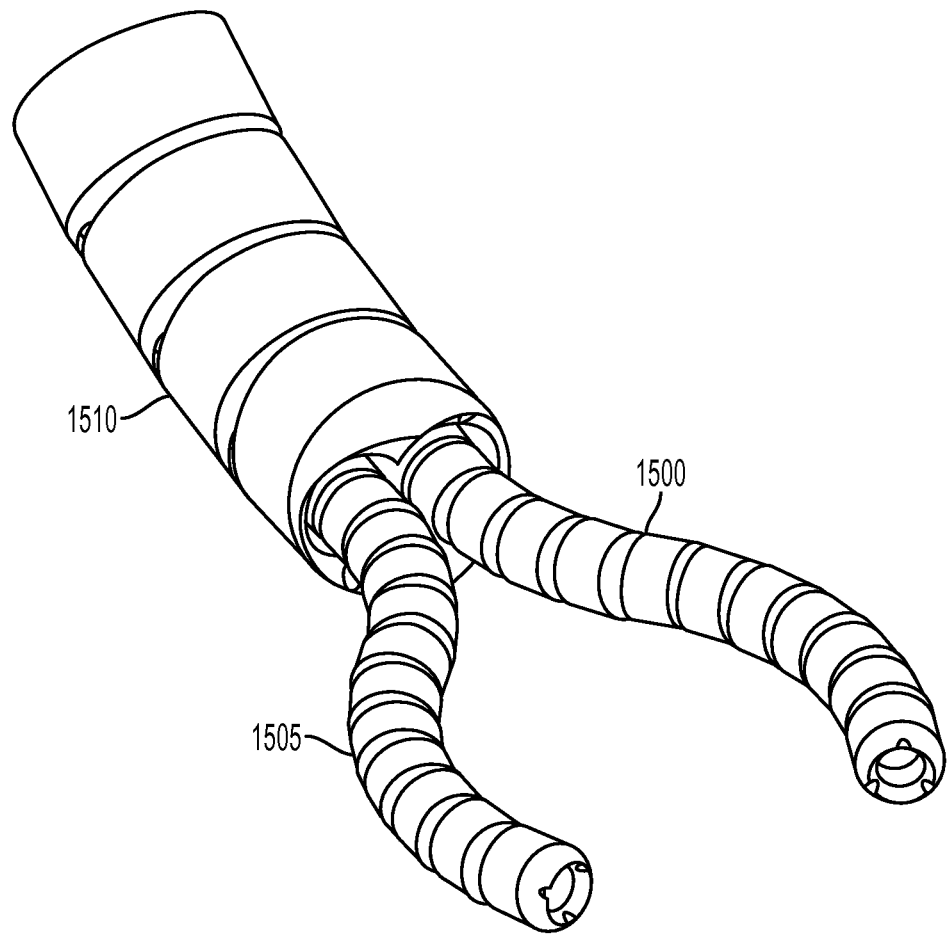
FIG. 10 illustrates exemplary steerable devices having an overtube according to an embodiment.

In an embodiment, an overtube may be used to deliver a plurality of flexible, snake-like devices 10 to a location as illustrated by FIG. 10. Although FIG. 10 illustrates an overtube surrounding two devices 1500, 1505 in a parallel configuration, additional devices and/or alternate configurations may be used within the scope of this disclosure.

In an embodiment, each device may be operated in a first mode, such as that described above. In an embodiment, each device may be operated in substantial unison with each of the other devices. For example, while in a limp state, a first device 1500 and a second device 1505 may advance into the overtube 1510 to a certain position. The first device 1500 and the second device 1505 may be made rigid, while the overtube 1510 may be made limp. The overtube 1510 may advance over the first device 1500 and the second device 1505.

In an embodiment, the devices 1510, 1505 and the overtube 1510 may operate in a second mode, similar to that described above. In an embodiment, the overtube 1510 may act as a steerable cannula that may be positioned with assistance from the first device 1500 and the second device 1505. For example, after reaching a target location, the overtube 1510 may be made rigid. The first device 1500 and second device 1505 may continue to advance, while the overtube 1510 may remain stationary. The first device 1500 and the second device 1505 may be independently operated as they advance beyond the overtube 1310. The overtube 1310 may provide additional length to the flexible, snake-like device 10, providing for more flexibility in its positioning and use. The overtube 1510 may also provide additional support to the first device 1500 and the second device 1500.

Figure 11:
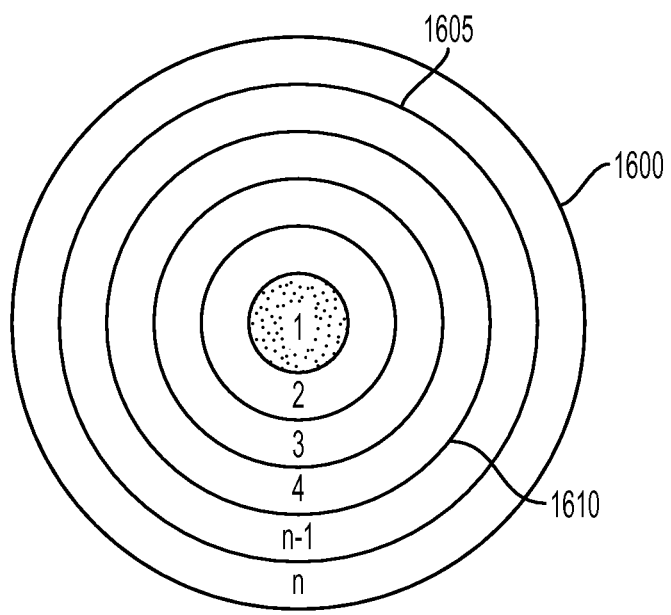
FIG. 11 illustrates an exemplary cross-section of a steerable multi-linked device according to an embodiment.

In an embodiment, a plurality of overtubes arranged in a nested structure may be used in conjunction with one or more devices. FIG. 11 illustrates a cross-section of the device having n-overtubes which are nested concentrically within each other according to an embodiment. As illustrated by FIG. 11, overtube n 1600 may surround at least a portion of overtube n−1 1605. Overtube n−1 1605 may in turn surround at least a portion of overtube 4 1610, and so on. As illustrated by FIG. 11, with a nested arrangement, either concentrically or eccentrically, of n-overtubes, a device may have a telescopic configuration. Any of the overtubes may be steerable or non-steerable, and those which are steerable will have a plurality of associate steering cables. Non-steerable devices require only a tensioning cable in a through-hole, and no steering cable. In an embodiment, the added support provided by additional overtubes may allow a device to reach lengths it otherwise would not be able to reach.

In an embodiment, a device may include one or more first mechanisms, one or more second mechanisms and/or one or more overtubes. The first mechanisms, second mechanisms and/or overtubes may be arranged in a nested, parallel and/or in any other configuration or combination of configurations. In an embodiment, one or more first mechanisms, second mechanisms and/or overtubes may be arranged concentrically, eccentrically and/or the like. For example, a first mechanism may be positioned concentrically relative to a second mechanism. Similarly, a device may be positioned eccentrically relative to an overtube.

In an embodiment, when a first mechanism is disposed eccentrically relative to a second mechanism, the first mechanism may "break out" of the channel through which it disposed during advancement when the device is highly curved. To resolve this problem, a passive section of inner links may be added to a distal end of the first mechanism. FIG. 12 illustrates an tensioning cable 1700 having a first cable portion 1705 and a second cable portion 1720 spliced together. For example, a hollow, braided cable 1700 may be used. In an embodiment, the distal end of the braided cable 1700 may be opened to form a sleeve 1715, and a shorter, separate section of the same type of cable may be inserted into the open weave of the sleeve 1715 as illustrated by FIG. 12. An active section of cable 1720 and a passive section 1705 may be combined such that their longitudinal axes are substantially aligned. After a portion of the shorter segment is inserted into the open braid of the longer cable, at least one running stitch 1710 may be run through both cables in the section where they overlap. In an embodiment, the portion may be approximately 3-5 mm long. In an embodiment, the stitch may secure the cables together.

In an embodiment, the increased diameter of the longer cable with the shorter cabled spliced into it may act as a force transmission point for the cable of the first mechanism on one of the intermediate links. The shorter section of cable may then have one or more links strung onto it. In an embodiment, three to five links may be strung onto the shorter section of cable. In an embodiment, the passive links may be secured with a stopper knot terminating the distal most end at the second link. Because the links of the active portion of the first mechanism may be secured between the feeder and the splice point, the intermediate links that are strung on the shorter section beyond the splice point may not be subject to the same loads. As such, these intermediate links may not become rigid.

In an embodiment, an additional benefit of having the cable spliced may be increased cable strength. For example, with a 150 lb test cable, the cable may break close to the knot at approximately 60 lbs. With a splice, however, the cable may break far from the termination point at approximately 100 lbs.

In an embodiment, a first mechanism, a second mechanism and/or an overtube may have any number of ports, through-holes and/or the like. In an embodiment, the ports and/or through-holes may be arranged such that they are radially symmetric, radially asymmetric and/or the like.

In an embodiment, placement of ports and/or through-holes relative to the first mechanism 12 and/or the second mechanism 14 may vary. For example, one or more ports may be placed concentrically or eccentrically on the device 10. In addition, one or more ports may be fully contained within one or more mechanisms of the device 10. For example, one or more ports may be fully contained within the second mechanism 14. Similarly, one or more ports may be fully contained within the first mechanism 12. In an embodiment, one or more ports may be split between a plurality of mechanisms of the device 10. For example, one or more ports may be split between the first mechanism 12 and the second mechanism 14. In such an embodiment, when the internal grooves of the second mechanism are substantially aligned with the external grooves of the first mechanism, a number of larger ports equal to the number of grooves on the first/second mechanism will be shared by the two mechanisms. In another embodiment, when the internal grooves of the second mechanism are substantially misaligned with the external grooves of the first mechanism, a number of smaller ports equal to twice the number of grooves on the first/second mechanism will exist. In an embodiment, one or more ports may be exposed to the exterior of a mechanism of the device 10. For example, one or more ports may be exposed to the exterior of the second mechanism 14. Additional and/or alternate port placements may be used within the scope of this disclosure.

Examples of different port and through-hole configurations are illustrated by FIGS. 13A-13J. For example, FIG. 13A illustrates an exemplary second mechanism 14 having four through-holes 1700, 1702, 1704, 1706. As illustrated by FIG. 13A, the through-holes may be eccentrically arranged in a radially symmetric manner. Steering cables may be delivered through the through-holes.

FIG. 13B illustrates an exemplary second mechanism 14 having three through-holes 1708, 1710, 1712 according to an embodiment. As illustrated by FIG. 13B, the through-holes 1708, 1710, 1712 may be arranged eccentrically in a radially symmetric manner inside the structure of the second mechanism 14.

FIG. 13C illustrates an exemplary second mechanism 14 having three ports 1714, 1716, 1718 contained in an outer wall 1720 of the second mechanism 14. The second mechanism 14 may also include one or more through-holes such as those 1713, 1715, 1717 illustrated by FIG. 13C. In an embodiment, the through-holes 1713, 1715, 1717 may be arranged eccentrically in a radially symmetric manner. In an embodiment, the through-holes may be evenly spaced within the arrangement of the ports 1714, 1716, 1718.

FIG. 13D illustrates an exemplary second mechanism 14 having three ports 1722, 1724, 1726 located on the exterior of the second mechanism 14. FIG. 13D also illustrates three through-holes 1764, 1766, 1768. In an embodiment, the three through-holes 1764, 1766, 1768 may support three steering cables. The through-holes 1764, 1766, 1768 may be arranged eccentrically in a radially symmetric fashion as illustrated by FIG. 13D. In an embodiment, the triangle that is formed may include a center point of a cross-section of a mechanism. For example, the triangle formed by the through-holes 1764, 1766, 1768 in FIG. 13D include a center point 1770 of the second mechanism 14. In an embodiment, the through-holes may be arranged as vertices of an equilateral triangle. In an embodiment, there may exist an even number of through-holes, such that each through-hole may have a corresponding through-hole located on the diametric opposite of a mechanism. In an embodiment, each through-hole and diametrically opposite through hole may oppose each other.

FIG. 13E illustrates an exemplary second mechanism 14 having two ports arranged eccentrically in a radially asymmetric manner 1728, 1730. As illustrated by FIG. 13E, the first mechanism 12 may be located eccentrically relative to the second mechanism 14. The ports 1728, 1730 may be located eccentrically relative to a first mechanism. As illustrated by FIG. 13E, the ports 1728, 1730 may be completely contained in the second mechanism 14. As such, no alignment/misalignment of the first mechanism and the second mechanism 14 may be necessary to define any plurality of ports 1728, 1730. As illustrated by FIG. 13E, the second mechanism 14 may include one or more through-holes 1727, 1729, 1731. The through-holes 1764, 1766, 1768 may be spaced to form a triangle as illustrated by FIG. 12E. In an embodiment, the through-holes 1764, 1766, 1768 may be wholly contained in the second mechanism 14.

FIG. 12F illustrates an exemplary first mechanism 12 having a single through-hole 1732 for, as an example, a tensioning cable. In an embodiment, the exemplary first mechanism 12 illustrated by FIG. 12F may correspond to the second mechanism 12 illustrated by FIG. 13E. If the through-hole is positioned concentrically, it is non-steerable, but is lockable when tension is applied. If the through-hole is positioned eccentrically, the first mechanism may be steerable, but not lockable.

FIG. 13G illustrates an exemplary first mechanism 12 having three through-holes 1734, 1736, 1738 for, as an example, three steering cables. In an embodiment, the first mechanism 12 and/or the second mechanism 14 may be steered with the steering cables. In contrast to a single through-hole configuration from FIG. 13F, the configuration depicted in FIG. 13G is both steerable and lockable.

FIG. 13H illustrates exemplary ports 1740, 1742, 1744 defined by a first mechanism 12 and a second mechanism 14. As illustrated by FIG. 12H, the ports 1740, 1742, 1744 may be located on an exterior portion of the first mechanism 12 and within the structure of the second mechanism 14.

FIG. 13I illustrates exemplary ports 1746, 1748, 1750 defined by a first mechanism 12. As illustrated by FIG. 12I, the ports 1746, 1748, 1750 may be located on an exterior portion of the first mechanism 12. In an embodiment, the first mechanism may have a single through-hole 1747 for, as an example, a tensioning cable.

FIG. 13J illustrates exemplary ports 1758, 1760, 1762 defined by a first mechanism 12. As illustrated by FIG. 13J, the ports may be located on an exterior portion of the first mechanism 12. The first mechanism 12 may also include one or more through-holes 1752, 1754, 1756. Additional and/or alternate port and through-hole locations may be used within the scope of this disclosure.

In an embodiment, a device 10 having two through-holes eccentrically arranged in a radially symmetric manner for steering cables may be capable of defining a 2D surface which is planar. In contrast, a device 10 having two through-holes for steering cables may be capable of defining a 2D surface which is non-planar if the through holes are radially asymmetric. In an embodiment, a device 10 having an odd number of radially symmetrically or asymmetrically arranged steering cables may require a dedicated actuator for each cable. For example, if a device 10 has a steering cables, where n is an odd number, or where n is an even number and the holes are arranged in a radially asymmetric fashion, n actuators may be necessary to load the n steering cables. In an embodiment, an actuator may be a device capable of providing a load, a force and/or the like. Exemplary actuators may include DC motors, stepper motors. EPAM devices, muscles, MicroElectricalMechanical systems ("MEMS") devices and/or the like.

For example, FIG. 13B illustrates a device 10 having three through-holes, each of which may support a steering cable. As the device in FIG. 13B has an odd number of steering cables (i.e., 3), each steering cable may require an actuator.

In an embodiment, a device 10 may have an even number of steering cables arranged in a radially symmetric manner. In an embodiment, each of the steering cables may have a corresponding actuator. Alternatively, diametrically opposing pairs of cables may be actuated with a single common actuator. For example, FIG. 13A illustrates a device 10 having four through-holes for four steering cables. A first steering cable associated with a first through-hole (e.g., 1700) may be located opposite a second steering cable associated with a second through-hole (e.g., 1704). The first steering cable and the second steering cable may be considered an opposing pair. In an embodiment, the first steering cable may be considered a counterpart to the second steering cable. In an embodiment, the first steering cable and the second steering cable may be loaded with a single actuator. In an embodiment, the number of actuators needed to load n steering cables (where n is an even number) may be a number greater than or equal to n and less than or equal to $$\frac{n}{2}$$

because each steering cable may have its own actuator or it may share an actuator with an opposing steering cable. An additional actuation element is necessary to simultaneously apply tension to all cables in order to lock the mechanism. In such an embodiment the total number of actuators necessary is $$\frac{n}{2}+1$$

In an embodiment, one or more steering cables may be arranged to maximize workspace. For devices 10 having an even number of steering cables, as one steering cable is made longer from the steering process, the length of its counterpart steering cable may be made shorter by an equal amount. For example, referring to FIG. 13A, a first steering cable associated with a first through-hole (e.g., 1700) may be located opposite a second steering cable associated with a second through-hole (e.g., 1704). As the first steering cable is made longer by x amount, the second steering cable may be made shorter by x amount.

While several embodiments of the invention have been described herein by way of example, those skilled in the art will appreciate that various modifications, alterations, and adaptations to the described embodiments may be realized without departing from the spirit and scope of the invention defined by the appended claims.

What is claimed is:

1. An articulated probe device, comprising:
a first mechanism comprising:
a first link positioned at a proximal area of the first mechanism,
a plurality of intermediate links, wherein a first one of the intermediate links is moveably coupled to the first link, and
a second link positioned at a distal area of the first mechanism which is moveably coupled to a second one of the intermediate links;
a second mechanism that concentrically surrounds at least a portion of the first mechanism, wherein the second mechanism comprises:
a first link positioned at a proximal area of the second mechanism,
a plurality of intermediate links, wherein a first one of the intermediate links is moveably coupled to the first link, and
a second link positioned at a distal area of the second mechanism and which is moveably coupled to a second one of the intermediate links; and
at least one overtube mechanism that concentrically surrounds at least a portion of the first mechanism and the second mechanism, wherein the overtube mechanism comprises:
a first link positioned at a proximal area of the overtube mechanism,
a plurality of intermediate links, wherein a first one of the intermediate links is moveably coupled to the first link, and
a second link which is moveably coupled to a second one of the intermediate links and positioned at a proximal area of the overtube mechanism,
wherein at least one of the first mechanism, second mechanism, and overtube mechanism is configured to be steerable and extendable beyond the other mechanisms
the first mechanism comprises a single concentrically positioned through-hole through which is disposed a tensioning cable;
a first end of the tensioning cable is configured to be terminated at an actuation component at the proximal area of the first mechanism; and
a second end of the tensioning cable is configured to be terminated at the second link of the first mechanism so that the tensioning cable transmits force to the second link of the first mechanism
The device further comprising a plurality of ports, each port partially formed by grooves within walls of the links of the first mechanism, and partially formed by structure of the walls of the links of the second mechanism or the overtube mechanism.

2. The device of claim 1, wherein the tensioning cable is configured to transmit force to one of the intermediate links of the first mechanism, so that at least some portion of the first mechanism exists in the rigid mode when the tensioning cable is under tension, and so that the first mechanism exists in a limp mode when the tensioning cable is not under tension.

3. The device of claim 1, wherein the first mechanism further comprises an eccentrically positioned through-hole through which is disposed an actuation cable wherein:
a first end of the actuation cable is configured to be terminated on an actuation component at the proximal area of the first mechanism, and
a second end of actuation cable as configured to be terminated at the second link of the first mechanism so that the cable transmits force to the second link of the first mechanism.

4. The device of claim 3, wherein the tensioning cable is configured to transmit force to one of the intermediate links of the first mechanism, so that at least some portion of the first mechanism develops a curvature as the length of the tensioning cable is changed in the direction of the eccentricity.

5. The device of claim 4, further comprising a plurality of ports that are completely contained within walls of the links of the first mechanism.

6. The device of claim 1, wherein the second mechanism further comprises:
at least two through-holes which are eccentrically arranged within the second mechanism, in a radially symmetric pattern; and
a plurality of actuation cables, wherein each cable is positioned to correspond to and pass through one of the through-holes, wherein at least one of the actuation cables having a first end and a second end is configured to be terminated on the second end at the second link of the second mechanism, and on the first end at an actuation component in the proximal area of the second mechanism.

7. The device of claim 6, wherein all of the actuation cables are configured to transmit forces to the second link of the second mechanism.

8. The device of claim 6, wherein all of the actuation cables transmit forces to at least one of the intermediate links of the second mechanism, such that the second mechanism exists in a limp mode when the actuation cables are slack, and at least some portion of the second mechanism exists in a rigid mode when all of the actuation cables are under equal tension.

9. The device of claim 6, wherein the actuation cables are configured so that changing the length of the actuation cables so that one is shorter than the other results in the development of a curvature in the second mechanism such that the curvature exists in a plane which is curving in the direction of the shorter of the actuation cables.

10. The device of claim 1, wherein the second mechanism further comprises:
    an even number of through-holes, greater than two, which are eccentrically arranged in a radially symmetric pattern through which are disposed actuation cables; and
    at least one of the actuation cables is configured to be terminated at a first end on the second link of the second mechanism, and at a second end and on a dedicated actuation component in the proximal area of the second mechanism.

11. The device of claim 6, wherein all of the actuation cables transmit forces to at least one of the intermediate links of the second mechanism, such that the second mechanism exists in a limp mode when the actuation cables are slack, and at least some portion of the second mechanism exists in a rigid mode when all of the actuation cables are under equal tension.

12. The device of claim 9, wherein the actuation cables are configured so that changing the length of the actuation cables results in the development of a curvature in the second mechanism such that the direction of the curvature is dependent on the lengths of the actuation cables.

13. The device of claim 1, wherein the second mechanism further comprises:
    an even number of through-holes, greater than two, which are eccentrically arranged within the second mechanism in a radially asymmetric pattern; and
    a plurality of actuation cables, wherein each cable is positioned to correspond to and pass through one of the through-holes,
    wherein at least one of the actuation cables having a first end and a second end is configured to be terminated on the first end at the second link of the second mechanism, and on the second end at an actuation component in the proximal area of the second mechanism.

14. The device of claim 13, wherein all of the actuation cables transmit forces to at least one of the intermediate links of the second mechanism, such that the second mechanism exists in a limp mode when the actuation cables are slack, and at least some portion of the second mechanism exists in a rigid mode when all of the actuation cables are under equal tension.

15. The device of claim 13, wherein the actuation cables are configured so that changing the length of the actuation cables results in the development of a curvature in the second mechanism such that the direction of the curvature is dependent on the lengths of the actuation cables.

16. The device of claim 6, wherein:
    the through-holes comprise an odd number of through-holes greater than two, which are eccentrically arranged in a radially symmetric pattern through which are disposed the actuation cables, and
    at least one of the actuation cables is configured to be terminated at a first end on the second link of the second mechanism, and at a second end and on a dedicated actuation component in the proximal area of the second mechanism.

17. The device of claim 16, wherein all of the actuation cables are configured to transmit forces to the second link of the second mechanism, and wherein all of the actuation cables transmit forces to at least one of the intermediate links of the second mechanism, such that the second mechanism exists in a limp mode when the actuation cables are slack, and at least some portion of the second mechanism exists in a rigid mode when all of the actuation cables are under equal tension.

18. The device of claim 16, wherein the actuation cables are configured so that changing the length of the actuation cables results in the development of a curvature in the second mechanism such that the direction of the curvature is dependent on the lengths of the actuation cables.

19. The device of claim 6, further comprising a plurality of ports that are completely contained within walls of the links of the second mechanism.

20. The device of claim 6, further comprising a plurality of ports, each port partially formed by grooves within walls of the links of the second mechanism, and partially formed by structure of the walls of the links of the first mechanism or the overtube.

21. The device of claim 1, wherein the overtube mechanism further comprises:
    at least two through-holes which are eccentrically arranged in a radially symmetric pattern through which are disposed actuation cables,
    wherein at least one of the actuation cables is configured to be terminated at a first end on the second link of the overtube mechanism and at a second end and on an actuation component at the proximate area of the overtube mechanism so that said actuation cable transmits force to the second link of the overtube mechanism.

22. The device of claim 21, wherein the actuation cables transmit forces to at least one of the intermediate links of the overtube mechanism so that the overtube mechanism exists in a limp mode when the actuation cables are slack, and so that at least a portion of the overtube mechanism exists in a rigid mode when all the actuation cables are under equal tension.

23. The device of claim 21, wherein the actuation cables are configured so that changing the length of the actuation cables results in the development of a curvature in the overtube mechanism such that the curvature exists in a plane containing the cables which is curving in the direction of the shorter cable.

24. The device of claim 21, wherein:
    the through-holes comprise an even number of through-holes, greater than two;
    all of the actuation cables are configured to connect and transmit forces to the second link of the overtube mechanism;
    all of the actuation cables are configured to connect and transmit forces to at least one of the intermediate links of the overtube mechanism; and
    the overtube mechanism is configured to exist in a limp mode when all of the actuation cables are slack, and in a rigid mode when all of the actuation cables are under equal amounts of tension.

25. The device of claim 24, wherein the overtube mechanism is configured so that changing the length of the actuation cables results in the development of a curvature in the overtube mechanism, wherein the direction of the curvature is dependent on the lengths of the actuation cables.

26. The device of claim 1, wherein the overtube mechanism further comprises:
an even number of through-holes greater than two, which are eccentrically arranged in a radially symmetric pattern through which are disposed actuation cables,
wherein at least one of the actuation cables is configured to be terminated at a first end on the second link of the overtube mechanism and at a second end and on an actuation component at the proximate area of the overtube mechanism so that said actuation cable transmits force to the second link of the overtube mechanism,
wherein actuation cables positioned opposite of each other terminate on a common actuation component.

27. The device of claim 26, wherein:
all of the actuation cables are configured to connect and transmit forces to at least one of the intermediate links of the overtube mechanism; and
the overtube mechanism is configured to exist in a limp mode when all of the actuation cables are slack, and in a rigid mode when all of the actuation cables are under equal amounts of tension; and
the overtube mechanism is also configured so that changing the length of the actuation cables results in the development of a curvature in the mechanism, wherein the direction of the curvature is dependent on the lengths of the actuation cables.

28. The device of claim 1, wherein the overtube mechanism further comprises:
an even number of through-holes, greater than two, which are eccentrically arranged in a radially asymmetric pattern through which are disposed actuation cables,
wherein at least one of the actuation cables is configured to be terminated at a first end on the second link of the overtube mechanism and at a second end and on a dedicated actuation component at the proximate area of the overtube mechanism so that said actuation cable transmits force to the second link of the overtube mechanism.

29. The device of claim 28, wherein:
all of the actuation cables are configured to connect and transmit forces to at least one of the intermediate links of the overtube mechanism; and
the overtube mechanism is configured to exist in a limp mode when all of the actuation cables are slack, and in a rigid mode when all of the actuation cables are under equal amounts of tension; and
the overtube mechanism is also configured so that changing the length of the actuation cables results in the development of a curvature in the mechanism, wherein the direction of the curvature is dependent on the lengths of the actuation cables.

30. The device of claim 1, wherein the overtube mechanism further comprises:
an odd number of through-holes, greater than two, which are eccentrically arranged in a radially symmetric pattern through which are disposed actuation cables,
wherein at least one of the actuation cables is configured to be terminated at a first end on the second link of the overtube mechanism and at a second end and on a dedicated actuation component at the proximate area of the overtube mechanism so that said actuation cable transmits force to the second link of the overtube mechanism.

31. The device of claim 30, wherein:
all of the actuation cables are configured to connect and transmit forces to at least one of the intermediate links of the overtube mechanism; and
the overtube mechanism is configured to exist in a limp mode when all of the actuation cables are slack, and in a rigid mode when all of the actuation cables are under equal amounts of tension; and
the overtube mechanism is also configured so that changing the length of the actuation cables results in the development of a curvature in the mechanism, wherein the direction of the curvature is dependent on the lengths of the actuation cables.

32. The device of claim 1, wherein the overtube mechanism further comprises a plurality of ports completely contained within walls of the links of the overtube mechanism.

33. The device of claim 1, wherein the overtube mechanism further comprises further comprising a plurality of ports, each port partially formed by grooves on m exterior lateral surface or an interior lateral surface of the links of the overtube mechanism.

34. The device from claim 1, wherein the first mechanism comprises grooves on an external lateral surface, such that each groove, along with surrounding structure of the second mechanism, defines a port.

35. The device from claim 1, wherein the second mechanism comprises grooves on an internal lateral surface, such that each groove, along with a groove-facing structure of the first mechanism, defines a port.

36. The device of claim 34 wherein the first mechanism with at least one external groove is properly aligned with a counterpart second mechanism with the same number of internal grooves to define a number of ports equal to the number of grooves on the first or second mechanism.

37. The device of claim 34, wherein the first mechanism with at least one external groove is misaligned with a counterpart second mechanism with the same number of internal grooves so that the second and overtube mechanisms define a number of ports equal to the total number of grooves on the first mechanism plus the second mechanism.

38. The device of claim 1, wherein the second mechanism comprises grooves on an external lateral surface such that each groove defines a port when the second mechanism is surrounded by the overture mechanism.

39. The device of claim 38, wherein the overtube mechanism comprises grooves on an interior lateral surface, and the second mechanism is properly aligned with the overtube mechanism so that the grooves match and define a number of ports equal to the number of grooves on the second mechanism.

40. The device of claim 38, wherein the overture mechanism comprises grooves on an interior lateral surface and the second mechanism is properly aligned with the overtube mechanism so that the second and overtube mechanisms define a number of ports equal to the total number of grooves on the overtube mechanism plus the second mechanism.

41. The device from claim 1, wherein at least one of the mechanisms comprises a rigid portion, at least one of the mechanisms comprises a steerable portion, and the steerable portion is configured to be extendible beyond a length of the rigid portion.

42. The device of claim 1, wherein the overtube mechanism is configured to advance over the first mechanism and the second mechanism when the first mechanism operates in a rigid mode.

43. The device of claim 1, wherein:
the first mechanism further comprises:
a first through-hole, and
a tensioning cable positioned to correspond to and pass through the first through-hole, the second mechanism further comprises:
  a plurality of second through-holes, and
  a plurality of actuation cables used to control movement of the second mechanism, wherein each actuation cable is positioned to correspond to and pass through one of the second through-holes, and
the at least one overtube mechanism further comprises:
  a plurality of overtube through-holes, and
  a plurality of overtube actuation cables used to control movement of the overtube, wherein each overtube actuation cable is positioned to correspond to and pass through one of the overtube through-holes.

\* \* \* \* \*